US011884979B2

(12) United States Patent
Sexton et al.

(10) Patent No.: US 11,884,979 B2
(45) Date of Patent: Jan. 30, 2024

(54) RNA BIOMARKERS FOR HEREDITARY ANGIOEDEMA

(71) Applicant: Takeda Pharmaceutical Company Limited, Osaka (JP)

(72) Inventors: Daniel J. Sexton, Melrose, MA (US); Malini Viswanathan, Acton, MA (US); Ryan Faucette, Melrose, MA (US); Tripti Gaur, South Grafton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 451 days.

(21) Appl. No.: 16/333,177

(22) PCT Filed: Sep. 15, 2017

(86) PCT No.: PCT/US2017/051772
§ 371 (c)(1),
(2) Date: Mar. 13, 2019

(87) PCT Pub. No.: WO2018/053260
PCT Pub. Date: Mar. 22, 2018

(65) Prior Publication Data
US 2019/0241961 A1    Aug. 8, 2019

Related U.S. Application Data

(60) Provisional application No. 62/395,811, filed on Sep. 16, 2016.

(51) Int. Cl.
| *C12Q 1/68* | (2018.01) |
| *C12Q 1/6883* | (2018.01) |
| *C12Q 1/6876* | (2018.01) |
| *G01N 33/50* | (2006.01) |
| *C12Q 1/6813* | (2018.01) |
| *C12Q 1/6851* | (2018.01) |
| *C12Q 1/686* | (2018.01) |

(52) U.S. Cl.
CPC .......... *C12Q 1/6883* (2013.01); *C12Q 1/686* (2013.01); *C12Q 1/6813* (2013.01); *C12Q 1/6851* (2013.01); *C12Q 1/6876* (2013.01); *G01N 33/502* (2013.01); *C12Q 2600/156* (2013.01); *C12Q 2600/158* (2013.01); *C12Q 2600/178* (2013.01); *G01N 2800/224* (2013.01)

(58) Field of Classification Search
None
See application file for complete search history.

(56) References Cited

U.S. PATENT DOCUMENTS

| 2006/0275313 A1 | 12/2006 | Clark et al. |
| 2007/0021589 A1 | 1/2007 | Collier et al. |
| 2007/0192882 A1 | 8/2007 | Dewald |
| 2009/0064350 A1 | 3/2009 | Dewald |
| 2010/0119512 A1 | 5/2010 | Feener et al. |
| 2011/0151430 A1 | 6/2011 | Kowalik et al. |
| 2013/0053275 A1 | 2/2013 | Knudsen |
| 2013/0102485 A1 | 4/2013 | Lee |
| 2013/0259839 A1 | 10/2013 | Aharonov et al. |
| 2013/0337479 A1 | 12/2013 | Uchida et al. |
| 2014/0162888 A1 | 6/2014 | Kuslich et al. |
| 2014/0213631 A1 | 7/2014 | Bhattacharjee et al. |
| 2017/0002094 A1 | 1/2017 | Sexton et al. |

FOREIGN PATENT DOCUMENTS

| CN | 1653080 A | 8/2005 |
| CN | 101495498 A | 7/2009 |
| CN | 104651513 A | 5/2015 |
| CN | 105517556 A | 4/2016 |
| CN | 105527419 A | 4/2016 |
| CN | 105873951 A | 8/2016 |
| JP | 2014-513528 A | 6/2014 |
| JP | 2016-144439 A | 8/2016 |
| WO | WO 2012/145363 A1 | 10/2012 |
| WO | WO 2014/036429 A1 | 3/2014 |
| WO | WO 2015/031679 A2 | 3/2015 |
| WO | WO 2015/037656 A1 | 3/2015 |
| WO | WO 2015/066611 A2 | 5/2015 |
| WO | WO 2015/179909 A1 | 12/2015 |
| WO | WO 2015/182781 A1 | 12/2015 |
| WO | WO 2016/020625 A1 | 2/2016 |
| WO | WO 2016/020626 A1 | 2/2016 |
| WO | WO 2016/023077 A1 | 2/2016 |
| WO | WO 2016/109774 A1 | 7/2016 |
| WO | WO 2016/139092 A1 | 9/2016 |

OTHER PUBLICATIONS

GeoPlatform Accession GPL15497, Applied Biosystems TaqMan Array Human MicroRNA Cards, Apr. 27, 2012, including full table listing, record obtained from https://www.ncbi.nlm.nih.gov/geo/query/acc.cgi?acc=GPL15497 on Jul. 29, 2021. (Year: 2012).*
Lopez-Lera et al. Orphanet Journal of Rare Diseases, 8:77; 12 pages (Year: 2013).*
Gao et al. Journal of Allergy and Clinical Immunology, p. AB32. Abstract #117 (Year: 2014).*
Cui et al. Cyclooxygenase-3 Gene Expression in Alzheimer's Hippocampus and in Stressed Human Neural Cells (2004) Neurochemical Research vol. 29, No. 9, 1731-1737 (Year: 2004).*
Ha et al. Interspecies Regulation of MicroRNAs and Their Targets (2008) Biochim Biophys Acta 1779(11): 735-742. (Year: 2008).*
McGee et al. Mitochondrial bioenergetics changes are induced by metabolic endotoxinaemia contributing to mitochondrial stress and dysfunction in human adipocytes (2011) Diabetologia 54:[Suppl1]S1-S542 (Year: 2011).*
Fu et al. Relationship between mitochondrial cytochrome oxidase mRNA expression and maternal inheritance of asthma (2013) Natl Med J China vol. 93, No. 28, Abstract (Year: 2013).*

(Continued)

*Primary Examiner* — Jehanne S Sitton
(74) *Attorney, Agent, or Firm* — Wolf, Greenfield & Sacks, P.C.

(57) ABSTRACT

Provided herein are methods and kits for analyzing a biological sample obtained from a subject having, suspected of having, or being at risk for a disease associated with the contact activation system.

26 Claims, 2 Drawing Sheets

Specification includes a Sequence Listing.

(56) References Cited

OTHER PUBLICATIONS

Oksuz et al. Therapeutic potential of cyclooxygenase-3 inhibitors in the management of glioblastoma (2016) J. Neurooncol. 126:271-278 (Year: 2016).*
Yu, et al. IgA nephropathy is associated with elevated urinary mitochondrial DNA copy numbers (2019) Nature Research, Scientific Reports 9:16068, 9 pages. (Year: 2019).*
Nagai et al. Changes in mitochondrial cytochrome c oxidase mRNA levels with cataract severity in lens epithelia of Japanese patients (2019) Molecular Medicine Reports 19:5464-5472. (Year: 2019).*
Lopez-Lera et al; Orphanet Journal of Rare Diseases, 8:77, 2013; pp. 1-12.*
Gao et al; J Allergy Clin Immunology, 2014, AB32 abstract 117.*
López-Lera et al., Disease-modifying factors in hereditary angioedema: an RNA expression-based screening. Orphanet J Rare Dis. May 20, 2013;8:77. doi: 10.1186/1750-1172-8-77.
Gao et al., Circulating Extracellular Micrornas in Hereditary Angioedema. J Allergy Clin Immunol. Feb. 2014;133(S2):AB32. Abstract 117. doi: 10.1016/j.jaci.2013.12.141.
Giavina-Bianchi et al., Brazilian Guidelines for Hereditary Angioedema Management—2017 Update Part 1: Definition, Classification and Diagnosis. Clinics (Sao Paulo). 2018;73:e310. doi: 10.6061/clinics/2018/e310. Epub May 3, 2018.
Kuśnierz-Cabala et al., Serum levels of unique miR-551-5p and endothelial-specific miR-126a-5p allow discrimination of patients in the early phase of acute pancreatitis. Pancreatology. Jul.-Aug. 2015;15(4):344-51. doi: 10.1016/j.pan.2015.05.475. Epub Jun. 6, 2015.
Zhu et al., Profiling maternal plasma microRNA expression in early pregnancy to predict gestational diabetes mellitus. Int J Gynecol Obstet. Jul. 2015;130(1):49-53. doi: 10.1016/j.ijgo.2015.01.010. Epub Mar. 23, 2015.
PCT/US2017/051772, Dec. 7, 2017, Invitation to Pay Additional Fees.
PCT/US2017/051772, Feb. 5, 2018, International Search Report and Written Opinion.
PCT/US2017/051772, Mar. 28, 2019, International Preliminary Report on Patentability.
Buyantseva et al., Update on treatment of hereditary angioedema. Asian Pac J Allergy Immunol. Jun. 2012;30(2):89-98.
Kelemen et al., Baseline level of functional C1-inhibitor correlates with disease severity scores in hereditary angioedema. Clin Immunol. Mar. 2010;134(3):354-8. doi: 10.1016/j.clim.2009.11.002. Epub Nov. 27, 2009.
Wang et al., The Intersection of the Kallikrein Kinin System and Fibrinolysis Coagulation System—Contact System, the Myth and Application. Medical Recapitulate. May 20, 2015;21(10):1740-1742.
Xu et al., Pathogenic Mechanism of Hereditary Angioedema. Chinese Journal of Allergy and Clinical Immunology. Jun. 30, 2012;6(2):125-130.

* cited by examiner

RNA BIOMARKERS FOR HEREDITARY ANGIOEDEMA

CROSS REFERENCE TO RELATED APPLICATIONS

This application is a national stage filing under 35 U.S.C. § 371 of international application number PCT/US2017/051772, filed Sep. 15, 2017, which claims the benefit under 35 U.S.C. § 1 19(e) of U.S. provisional application No. 62/395,811, filed Sep. 16, 2016. The entire contents of each of these referenced applications are incorporated by reference herein.

BACKGROUND

The plasma contact activation system is a pro-inflammatory and pro-coagulant system involving a group of plasma proteases. It is activated by either factor XIIa upon exposure to foreign or negatively charged surfaces or on endothelial cell surfaces by prolylcarboxypeptidases (Sainz I. M. et al., *Thromb. Haemost.* (2007) 98, 77-83). Inappropriate or unregulated activation of the contact system has been implicated in various diseases, including hereditary angioedema (HAE).

HAE is a disease that causes episodic attacks of swelling, which can affect multiple parts of the body such as the face, extremities, genitals, GI tract and upper airways. Because HAE symptoms often resemble symptoms of allergies or intestinal colics, HAE patients are often difficult to identify until they exhibit severe or life-threatening symptoms. Early diagnosis would allow for better management of emergency situations involving acute HAE attacks and would also help manage HAE patients to prevent or dampen acute HAE episodes, e.g., allowing an HAE sufferer to avoid exposure to stimuli that might trigger HAE episodes.

It is therefore of great interest to identify biomarkers for HAE and develop reliable diagnostic and prognostic methods for identifying subjects having certain types of HAE or being at risk of suffering an acute HAE attack. Such biomarkers would also benefit the studies on disease mechanisms, which could facilitate the development of effective new therapies for the disease.

SUMMARY OF THE PRESENT DISCLOSURE

The present disclosure is based on the identification of RNA biomarkers that are differentially present in biological samples obtained from subjects having diseases associated with the contact activation system as compared to healthy individuals and/or differentially present in biological samples obtained from subjects in different disease states (e.g., attack versus basal).

Accordingly, one aspect of the present disclosure provides methods of analyzing a sample comprising (i) providing a biological sample (e.g., serum sample or a plasma sample) obtained from a subject, such as a human subject, having, suspected of having, or being at risk for a disease associated with the contact activation system; and (ii) measuring the level of a RNA biomarker set, which comprises at least one RNA biomarker selected from Table 1, wherein if the biomarker set consists of one RNA biomarker, said RNA biomarker is not hsa-miR-16-5p, hsa-miR-17-5p, hsa-miR-19a-3p, or hsa-miR-20a-5p. In some embodiments, the disease associated with the contact activation system is hereditary angioedema (HAE), such as type 1 HAE or type II HAE.

In some embodiments, the biomarker set consists of 2-10 RNA biomarkers selected from Table 1. In some embodiments, the RNA biomarker is a messenger RNA encoding a mitochondrial protein, which can be mitochondrially-encoded cytochrome C oxidase III (MT-CO3) or mitochondrially-encoded oxidoreductase core subunit (MT-ND3). In some embodiments, the RNA biomarker is a microRNA (e.g., hsa-miR-423-3p, hsa-miR-1307-3p, hsa-miR-355-3p, hsa-miR-485-5p, hsa-miR-16-5p, hsa-miR-19a-3p, hsa-miR-20a-5p, hsa-miR-17-5p, hsa-miR-885-5p, hsa-miR-335-3p, hsa-miR-485-5p).

In some embodiments, the level of a RNA biomarker set can be measured by a process involving polymerase chain reaction and/or nucleic acid hybridization.

In some embodiments, the method further comprises identifying the subject as having a disease associated with the contact system, if the level of the RNA biomarker set of the subject deviates from the level of the same RNA biomarker set of a control subject. In some embodiments, the method further comprises administering to the subject an effective amount of a therapeutic agent for treating the disease, such as a plasma kallikrein (pKal) inhibitor, a bradykinin 2 receptor inhibitor, and/or a C1 esterase inhibitor, if the subject is identified as having the disease. In some embodiments the pKal inhibitor is an anti-pKal antibody (e.g., lanadelumab) or an inhibitory peptide (e.g., ecallantide). In some examples, the bradykinin 2 receptor inhibitor is an inhibitory peptide (e.g., icatibant). In some examples, the C1 esterase inhibitor is a human plasma-derived C1 esterase inhibitor.

In some embodiments, the subject is a human patient who is on a treatment for the disease, and wherein the method further comprises assessing the efficacy of the treatment based on the level of the RNA biomarker set, a deviation of the level of the RNA biomarker set of the subject from that of a control subject being indicative of the treatment efficacy. In some embodiments, the method further comprises identifying a suitable treatment for the subject based on the level of the RNA biomarker set. In some embodiments, the method further comprises identifying the subject as a candidate for a treatment of the disease based on the level of the RNA biomarker set.

In some embodiments, the RNA biomarker set comprises on or more RNA biomarkers selected from the group consisting of hsa-miR-1307-3p, hsa-miR-335-3p, and hsa-miR-485-5p. In some embodiments, the method further comprises assessing the risk of disease attack in the subject based on the level of the RNA biomarker set, a deviation of the RNA biomarker set level of the subject from that of a control subject being indicative of the risk of a disease attack.

The present disclosure provides RNA biomarkers capable of identifying patients with diseases associated with the contact activation system (e.g., HAE). Measuring the levels of the biomarker sets may also be useful in the evaluation and treatment of such diseases.

In another aspect, a kit is provided for analyzing a sample of a subject having, suspected of having, or at risk for a disease associated with the contact system, the kit comprising a first binding agent specific to a first RNA biomarker selected from Table 1; and a second binding agent specific to a second RNA biomarker selected from Table 1; wherein the first RNA biomarker and the second RNA biomarker are different. In some examples, the first binding agent is an oligonucleotide complementary (completely or partially) to the first RNA biomarker and/or the second binding agent is an oligonucleotide complementary (completely or partially) specific to the second RNA biomarker. The first binding agent and the second binding agent may be immobilized on a support member. In some instances, the first binding agent and/or the second binding agent is conjugated to a label (e.g., fluorescent label).

The details of one or more embodiments of the present disclosure are set forth in the description below. Other features or advantages of the present disclosure will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION

Figure 1:
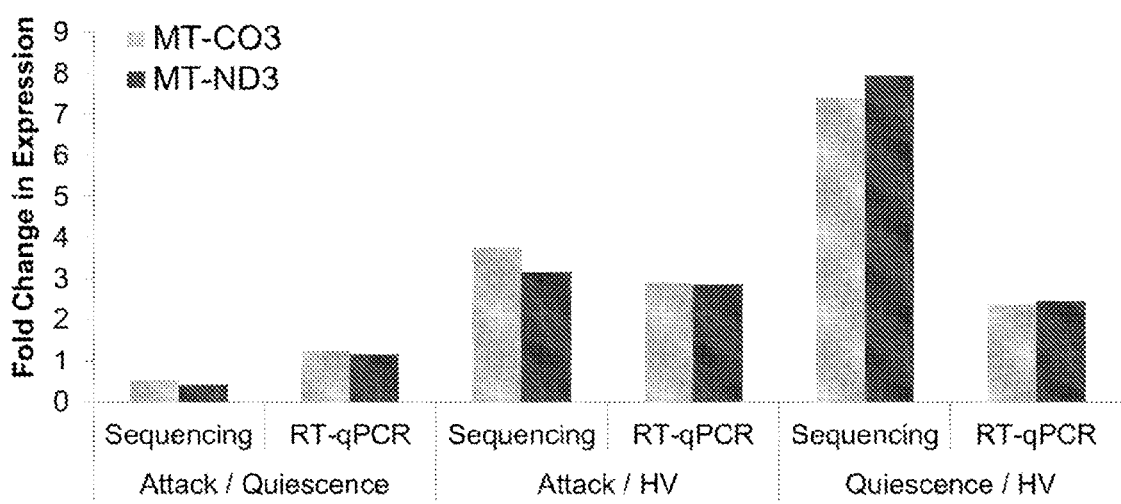
FIG. 1 is a graph showing increased transcript levels for mitochondrial cytochrome oxidase (MT-CO3) and mitochondrial NADH dehydrogenase (MT-ND3) during both HAE in quiescence (HAE during basal state) and HAE during attack. The fold change of each transcript is shown as measured by sequencing and by RT-qPCR.

The contact activation system initiates the intrinsic pathway of coagulation and promotes inflammation through the release of the proinflammatory peptide bradykinin. Factor XII (FXII), also known as Hageman Factor, is a serine protease that plays a role in activation of the intrinsic pathways of coagulation as well as the kallikrein-kinin system. FXII is activated by negatively charged surfaces (e.g., polyanionic surfaces, glass, polyphosphate, ellagic acid) to produce the active form FXIIa. Activated FXIIa has the ability to cleave pre-kallikrein, generating active pKal. Subsequently, activated pKal is able to cleave FXII into FXIIa, resulting in a positive feedback loop in which FXIIa generates even more pKal, which further activates additional FXII into FXIIa. Activated pKal is also able to cleave high molecular weight kininogen (HMWK) to release bradykinin. In diseases associated with contact system activation, such as HAE, increased levels of bradykinin can induce vasodilation and inflammation that result in edematous HAE attacks. It is desired to identify novel biomarkers that can be used, for example, to identify diseases as mediated by the contact activation system, identify subjects having or being at risk of having such a disease.

The present disclosure is based, at least in part, on the identification of nucleic acids (RNAs, e.g., microRNAs and RNA transcripts encoding proteins) that are differentially present in biological samples obtained from subjects having diseases associated with the contact activation system (e.g., basal or attack) as compared to healthy individuals via transcriptomic analysis. Furthermore, several RNAs (e.g., microRNA biomarkers) were identified as differentially present in biological samples obtained from subjects during an attack of a disease of the contact activation system as compared to subjects having the disease at quiescent (basal) state.

Accordingly, provided herein are methods for analyzing biological samples from subjects having, suspected of having, or being at risk for a disease associated with the contact activation system (e.g., HAE) by detecting the presence or measuring the level of a RNA biomarker set. Such methods may be useful, e.g., for identifying patients who are at risk of a disease associated with the contact activation system (e.g., HAE), selecting a candidate for treatment, monitoring disease progression or disease state, assessing the efficacy of a treatment against a disease, determining a course of treatment, assessing whether a subject is at risk for an attack of the disease, identifying whether a disease or disorder is associated with the contact activation system, and/or for research purposes, including, e.g., studying the mechanism of a disease and/or biological pathways/processes involved in the disease, which may be relied upon for the development of new therapies.

Contact Activation System RNA Biomarkers

The methods and kits described herein are based, at least in part, on the identification of RNAs that were found to be differentially present in samples from subjects having HAE as compared with samples from healthy subjects, and/or differentially present in samples at different stages of such a disease (e.g., basal versus attack). As used herein, the term "RNA biomarker" or "RNA biomarker set" refers to a RNA or set of RNAs that are present at different levels in samples from different groups of subjects, for example, subjects having a disease associated with the contact system versus healthy subjects (e.g., subjects who are free of the disease), or subjects having the disease and being at the quiescence stage versus subjects under the attack of the disease. Such biomarker/biomarker sets may be used in both diagnostic/prognostic applications and non-clinical applications, for example, for research purposes.

In some embodiments, a RNA biomarker may be present at an elevated level in samples from subjects having a disease associated with the contact activation system (e.g., HAE) as compared to the level of the same RNA biomarker in samples from healthy subjects. In some embodiments, a RNA biomarker may be present at a reduced level in samples from subjects having a disease associated with the contact activation system (e.g., HAE) as compared to the level of the biomarker in samples from healthy subjects. In yet other instances, a RNA biomarker may be present at an elevated level in samples obtained from subjects under attack of a disease as described herein as compared with subjects during disease quiescence. Alternatively, a RNA biomarker may be present at a reduced level in samples obtained from subjects under attack of a disease as described herein as compared with subjects during disease quiescence.

In some embodiments, a RNA biomarker set containing one or more biomarkers can be analyzed in the methods described herein. When the RNA biomarker set contains more than one biomarker, all of the biomarkers may present at elevated levels or reduced levels in subjects having a disease as compared with health subjects. Alternatively, a RNA biomarker set may contain at least one biomarker that is elevated in subjects having the disease as compared with healthy subjects and at least one biomarker that is reduced in subjects having the disease as compared with healthy subjects.

Similarly, a RNA biomarker set for differentiating subjects under attack of a disease from subjects in disease quiescence, the biomarker set may contain multiple biomarkers that are all elevated or reduced in a first disease stage (e.g., attack) as compared with a second disease stage (e.g., quiescence). Alternatively, the biomarker set may contain at least one biomarker that is elevated in the first disease stage as compared with the second disease stage and at least one biomarker that is reduced in the first disease stage as compared with the second disease stage.

Table 1 below provides RNA biomarkers that can be evaluated by the methods described herein evaluate subjects or biological samples from subjects for diseases associated with the contact activation system.

TABLE 1

Contact System Activation Biomarkers

| RNA Grouping | RNA Biomarker |
|---|---|
| Mitochondrial Function | Mitochondrially-Encoded Cytochrome C Oxidase III (MT-CO3) |
| | Mitochondrially-Encoded NADH-Ubiquinone Oxidoreductase Core Subunit 3 (MT-ND3) |
| MicroRNA | Hsa-miR-423-3p |
| | Hsa-miR-1307-3p* |
| | Hsa-miR-485-5p |
| | Hsa-miR-16-5p |
| | Hsa-miR-19a-3p |
| | Hsa-miR-20a-5p |
| | Hsa-miR-17-5p |
| | Hsa-miR-885-5p |
| | Hsa-miR-335-3p* |
| | Hsa-miR-485-5p* |

*Indicates RNAs that were identified as being differentially present in samples from HAE patients during an attack as compared to HAE patients during quiescence.

In some embodiments, the biomarker set to be measured and analyzed in any of the methods described herein includes at least one (e.g., 1, 2, 3, 4, 5, 6, 7, 8, 9, 10, or more) RNAs selected from Table 1. When the biomarker set includes a single RNA biomarker, that RNA biomarker may not be hsa-miR-16-5p, hsa-miR-17-5p, hsa-miR-19a-3p, or hsa-miR-20a-5p. In some examples, the RNA biomarker set to be measured and analyzed in a method described herein does not include a combination of any one of hsa-miR-16-5p, hsa-miR-17-5p, hsa-miR-19a-3p, and hsa-miR-20a-5p.

As described in Example 1, it was unexpectedly found that several RNAs encoding proteins involved in similar cellular processes and pathways were differentially present in samples from subjects having HAE as compared to healthy subjects. This data indicates that the RNAs shown in Table 1 may play a role in or be affected by diseases associated with the contact system.

The RNA biomarkers described herein may be characterized as "involved in" or "associated with" a particular pathway or activity. As used herein, the terms "involved in" or "associated with" refer to a RNA that contributes to pathway. For example, a RNA, such as an RNA that encodes a protein or a microRNA, that is involved in or associated with a pathway may perform a function within the pathway (e.g., regulate expression of another nucleic acid or activity of a protein) or encode a molecule (e.g., a protein) that performs a function within the pathway or cellular process.

In some embodiments, the RNA biomarker set includes one or more RNAs that encode mitochondrial proteins as listed in Table 1.

In some embodiments, the RNA biomarker set includes one or more microRNA, e.g., one or more microRNAs selected from Table 1.

As also described in Example 1, it was also found that several RNAs were differentially present in samples from subjects having HAE during an HAE attack as compared to subjects having HAE during quiescence (basal). In some embodiments, the biomarker set includes one or more microRNA, e.g., one or more microRNA selected from Table 1.

Utilities of the RNA Biomarkers

One aspect of the present disclosure relates to methods for analyzing samples obtained from subjects (e.g., human patients) having, suspected of having, or being at risk for a disease associated with the contact activation system by measuring the level of a biomarker set as described herein in the sample. Results obtained from such assay methods would be useful for diagnostic and/or prognostic purposes, as well as for other non-clinical purposes, such as research purposes.

(i) Analysis of Biological Samples

The methods described herein involved providing a biological sample obtained from a subject. As used herein, a "biological sample" refers to a composition that comprises tissue, e.g., blood, plasma or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is a body fluid sample such as a serum or plasma sample. In some embodiments, multiple (e.g., at least 2, 3, 4, 5, or more) biological samples may be collected from subject, over time or at particular time intervals, for example to assess the disease progression or evaluate the efficacy of a treatment.

A biological sample can be obtained from a subject using any means known in the art. In some embodiments, the sample is obtained from the subject by collecting the sample (e.g., a blood sample) into an evacuated collection tube (e.g., an evacuated blood collection tube). In some embodiments, the evacuated collection tube contains one or more protease inhibitors, for example, to reduce or prevent ex vivo activation of the contact system during sample collection. Such protease inhibitors may be contained in a liquid formulation. In some embodiments, the protease inhibitors comprise at least one serine protease inhibitor and at least one cysteine protease inhibitor. Such evacuated collection tubes are known in the art. See, for example, PCT Application No. US2016/046681. Optionally, an evacuated blood collection tube may further comprise one or more anti-coagulants.

The terms "patient," "subject," or "individual" may be used interchangeably and refer to a subject who needs the analysis as described herein. In some embodiments, the subject is a human or a non-human mammal. In some embodiments, a subject is suspected of or is at risk for a disease or disorder associated with the contact activation system (e.g., HAE). Such a subject may exhibit one or more symptoms associated with the disease. Alternatively or in addition, such a subject may carry one or more risk factors for the disease, for example, a genetic factor associated with the disease (e.g., a genetic defect in CI-INH).

Alternatively, the subject who needs the analysis described herein may be a patient of the disease. Such a subject may be under the attack of the disease currently, or may suffer from the disease in the past (e.g., during disease quiescence currently). In some examples, the subject is a human patient who may be on a treatment of the disease, for example, a treatment involving a C1 esterase inhibitor (C1-INH), a plasma kallikrein inhibitor, or a bradykinin inhibitor. In other instances, such a human patient may be free of such a treatment.

Examples of diseases associated with the contact activation system include, without limitation, kallikrein-mediated disorders, e.g., a bradykinin-mediated disorder, such as hereditary angioedema (HAE), non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g., anaphylaxis, asthma, chronic obstructive pulmonary disease, acute respiratory distress syndrome, cystic fibrosis, persistent, rhinitis), and tissue injuries (e.g., burn or chemical injury).

In some embodiments, the disease or condition that is associated with the contact activation system is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with HAE develop a non-itchy rash called erythema marginatum during an attack.

Swelling of the airway can be life threatening and causes death in some patients. Mortality rates are estimated at 15-33%. HAE leads to about 15,000-30,000 emergency department visits per year. Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When HAE is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., *J Allergy Clin Immunol*, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert (CSL Behring), which is pasteurized, was approved by the F.D.A. in 2009 for acute attacks. CINRYZE®, which is nanofiltered, was approved by the F.D.A. in 2008 for prophylaxis. Rhucin/Ruconest (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol*, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal. The present disclosure is based, at least in part, on the identification of RNAs that have differential levels in samples from HAE patients as compared to healthy individuals (Table 1). Measuring the levels of biomarker sets of these RNAs can be used to identify whether a subject has a disease, such as HAE. In some embodiments, the methods may be used to determine whether a patient has had or is having an HAE attack.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient.* 2012;5(2): 113-26.

The biological sample described herein can be subject to analysis by measuring the level of a RNA biomarker set as described herein in the biological sample. Levels (e.g., the amount) of a biomarker disclosed herein, or changes in levels the biomarker, can be assessed using assays described herein and/or assays known in the art. One or more of the biomarkers described herein may be analyzed using convention methods, for example, PCR, nucleic acid hybridization, or microarray. In some embodiments, the level of a biomarker is assessed or measured by directly detecting the RNA biomarker in a biological sample. In some embodiments, the RNA biomarker may be amplified by, e.g., PCR, before detection.

The type of detection assay used for the detection and/or quantification of a contact activation system biomarker such as those provided herein will depend on the particular situation in which the assay is to be used (e.g., clinical or research applications), and on the kind and number of biomarkers to be detected, and on the kind and number of patient samples to be run in parallel, to name a few parameters.

In some embodiments, the biomarker is directly measured in the biological sample, for example by contacting the sample with a binding agent that selectively binds to one or more of the RNA biomarkers (e.g., any one of the biomarkers provided in Table 1). In some embodiments, the biomarker (the RNA or cDNA corresponding to the RNA biomarker) is detected using a hybridization method, such as contacting the sample with a nucleic acid probe that specification binds to the biomarker, Southern blotting, or Northern blotting methods.

In some embodiments, the binding agent is an oligonucleotide that is complementary to a RNA biomarker. The oligonucleotides for use in the methods described herein are oligonucleotides (single-strand DNA or RNA molecules) that are complementary (partially or completely) to a region of the RNA biomarker (or a cDNA corresponding to the RNA biomarker).

"Complementary," as used herein, refers to the nucleobase complementarity commonly known in the art. For example, adenine is complementary to thymine (in DNA) or uracil in RNA; and guanine is complementary to cytosine. "Sequence complementarity", or "nucleic acid sequences being complementary to one another", as used herein, means when the two nucleic acid molecules are aligned antiparallel to each other, the nucleotide bases at each position, or at most positions in the sequences are complementary, and that the two nucleic acid molecules can hybridize and form a duplex under suitable conditions, e.g., hybridization temperature. As known in the art, a sequence complementarity needs not be 100% for the two nucleic acid molecules to hybridize and form a duplex. The sequence complementarity between the oligonucleotide and the RNA biomarker (or a cDNA corresponding to the RNA biomarker) may be at least 80% complementary to the corresponding region in the RNA biomarker. In some embodiments, the oligonucleotide contains a fragment that is at least 80% (e.g., 85%, 90%, 95%, 98%, or 100%) complementary to a portion of the RNA biomarker (or cDNA corresponding to the RNA biomarker). In some instances, the oligonucleotide contains a fragment that is completely complementary (100% complementary) to a portion of the RNA biomarker (or cDNA corresponding to the RNA biomarker). Such an oligonucleotide may be used in differentiating the RNA biomarker from substantially similar nucleic acids, for example, nucleic acids having 1, 2, or 3 base differences relative to the target nucleic acid.

The oligonucleotide may contain up to 100 nucleotides (e.g., up to 80 nt, 60 nt, 50 nt, or 30 nt). In some embodiments, the oligonucleotide may be 8-50 nucleotides in length, e.g., 8-40, 8-30, 10-30, 15-30, or 15-20 nucleotides in length. In some examples, the oligonucleotide may be 10, 11, 12, 13, 14, 15, 16, 17, 18, 19, 20, 21, 22, 23, 24, 25, 26, 27, 28, 29, or 30 nucleotides in length. In some examples, the whole molecule of the oligonucleotide is complementary to a portion of a RNA biomarker. In other examples, a fragment of oligonucleotide is complementary to a portion of a RNA biomarker. For example, an oligonucleotide may contain a linker (e.g., a poly A or poly T linker) for attaching to a support member. Alternatively or in addition, a detecting probe may contain such a linker for conjugating to a label. The fragment of an oligonucleotide that is complementary to a portion of a RNA biomarker may be located at the 5' end of the oligonucleotide, the 3' end of the oligonucleotide, or in the middle of the oligonucleotide. In some embodiments, the fragment of the oligonucleotide that is complementary to the RNA biomarker may be at least 10-nucleotide long (e.g., at least 12, 15, 18, 20, or 25-nucleotide long).

In some embodiments, the oligonucleotide comprises one or more modified nucleotides, for example, containing nucleotides modified by a 2'-O-methoxyl group, a 2'-O-methoxyethyl group, and/or a phosphorothioate group. In some examples the oligonucleotide comprises one or more locked nucleic acids (LNAs). An LNA, often referred to as inaccessible RNA, is a modified RNA nucleotide, in which the ribose moiety is modified with an extra bridge connecting the 2' oxygen and 4' carbon. This bridge "locks" the ribose in the 3'-endo (North) conformation, which is often found in the A-form duplexes. LNA nucleotides can be used in both DNA and RNA probes. In some examples, up to 50%

(e.g., 40%, 30%, 20%, or 10%) of the nucleotides in the probe are LNAs. In some examples, an oligonucleotide may comprise 10, 8, 6, 5, 4, 3, 2, or 1 LNA.

The oligonucleotide can be designed based on the sequence of the RNA biomarker for which detection is desired and be prepared via conventional methods, for example, chemical synthesis or in vitro transcription.

The oligonucleotide as described herein can be immobilized on a support member via a conventional method. As used herein, "immobilized" means attached, bound, or affixed, covalently or non-covalently, so as to prevent dissociation or loss of the oligonucleotide, but does not require absolute immobility with respect to either the oligonucleotide or the support member. A support member can be a solid or semi-solid member with a surface that can be used to specifically attach, bind or otherwise capture a nucleotide probe (e.g., the oligonucleotide of the present disclosure), such that the nucleotide probe becomes immobilized with respect to the support member.

The support member of the present disclosure may be fabricated from one or more suitable materials, for example, plastics or synthetic polymers (e.g., polyethylene, polypropylene, polystyrene, polyamide, polyurethane, phenolic polymers, or nitrocellulose), naturally derived polymers (e.g., latex rubber, polysaccharides, polypeptides), composite materials, ceramics, silica or silica-based materials, carbon, metals or metal compounds (e.g., comprising gold, silver, steel, aluminum, or copper), inorganic glasses, silica, and a variety of other suitable materials. Non-limiting examples of potentially suitable configurations include beads (e.g., magnetic beads), tubes (e.g., nanotubes), plates, disks, dipsticks, chips, microchips, coverslips, or the like.

The surface of the support member of the present disclosure may comprise any molecule, other chemical/biological entity, or solid support modification disposed upon the solid support that can be used to specifically attach, bind or otherwise capture a nucleic acid molecule (e.g., an oligonucleotide complementary to an RNA biomarker). Surface compositions that may be used to immobilize a nucleic acid molecule can be readily found in the art. For example, the surface may comprise a complementary nucleic acid or a nucleic acid binding protein, which can be attached to the surface via convention methods. Thus, the linkage between the nucleic acid to be immobilized (e.g., the oligonucleotide of the present disclosure) and the surface may comprise one or more chemical or physical (e.g., non-specific attachment via van der Waals forces, hydrogen bonding, electrostatic interactions, hydrophobic/hydrophilic interactions; etc.) bonds and/or chemical linkers providing such bond(s). Alternatively, the surface of the support member may comprise reactive functional groups that are capable of forming covalent bonds with the nucleic acid molecules to immobilized. In some embodiments, the functional groups are chemical functionalities. That is, the binding surface may be derivatized such that a chemical functionality is presented at the binding surface, which can react with a chemical functionality on the nucleic acid to be captured, resulting in attachment. Examples of functional groups for attachment that may be useful include, but are not limited to, amino groups, carboxyl groups, epoxide groups, maleimide groups, oxo groups, and thiol groups. Functional groups can be attached, either directly or through the use of a linker, the combination of which is sometimes referred to herein as a "crosslinker." Crosslinkers for attaching nucleic acid molecules to a support member are known in the art; for example, homo-or hetero-bifunctional crosslinkers as are well known (e.g., see 1994 Pierce Chemical Company catalog, technical section on crosslinkers, pages 155-200, or "Bioconjugate Techniques" by Greg T. Hermanson, Academic Press, 1996). Non-limiting example of crosslinkers include alkyl groups (including substituted alkyl groups and alkyl groups containing heteroatom moieties), esters, amide, amine, epoxy groups and ethylene glycol and derivatives. A linker may also be a sulfone group, forming a sulfonamide. In some embodiments, the functional group is a light-activated functional group. That is, the functional group can be activated by light to attach the capture component to the capture object surface. One example is PhotoLink™ technology available from SurModics, Inc. in Eden Prairie, MN.

It is to be understood that the examples provided herein on the support member and the surface composition are not meant to be limiting. Any support members that are known in the art to be suitable for immobilization of nucleic acid molecules may be used in accordance with the methods and kits described herein.

In some embodiments, the binding agent (e.g., oligonucleotide complementary to a RNA biomarker) may be conjugated to a label. "Conjugated", as used herein, means the label is attached to the binding agent, covalently or non-covalently. The label agent can be any molecule, particle, or the like, that facilitates detection, directly or indirectly, using a suitable detection technique. In the case of direct detection, the labeling agent may be a molecule or moiety capable of releasing a signal that can be directly interrogated and/or detected (e.g., a fluorescent label or a dye). In a non-limiting example of indirect detection, the label may be a molecule or moiety capable of converting a substrate (e.g., an enzyme) to a product that is capable of releasing a detectable signal. For example, the label may be a luciferase, which converts luciferin to oxyluciferin to emit detectable lights. In another non-limiting example of indirect detection, the label is a binding ligand to a molecule or moiety capable of converting a substrate (e.g., an enzyme), wherein the converted substrate releases detectable signals.

In some embodiments, the label is a fluorescent label. Examples include, but are not limited to, fluorescein, isothiocyanate, rhodamine, phycoerythrin, phycocyanin, allophycocyanin, o-phthaldehyde, fluorescamine and fluorescent metals such as $^{152}$Eu or other metals from the lanthanide series, CYE dyes, and fluorescent proteins such as eGFP, eYFP, eCFP, mKate2, mCherry, mPlum, mGrape2, mRaspberry, mGrape1, mStrawberry, mTangerine, mBanana, and mHoneydrew.

Other exemplary labels include, but are not limited to, biotin, phosphorescent labels, chemiluminescent labels or bioluminescent labels (such as luminal, isoluminol, theromatic acridinium ester, imidazole, acridinium salts, oxalate ester, and dioxetane), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99}$Tc, $^{123}$I, $^{111}$In, $^{131}$I, $^{97}$Ru, $^{67}$Ga, and $^{68}$Ga. Other examples include chromophores and enzymes (e.g., malate dehydrogenase, staphylococcal nuclease, delta-V-steroid isomerase, yeast alcohol dehydrogenase, alpha-glycerophosphate dehydrogenase, triose phosphate isomerase, peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase).

In some embodiments, the biomarker is measured using polymerase chain reaction. In some embodiments, RNA extracted from the biological sample is subjected to polymerase chain reaction. In some embodiments, cDNA corresponding to the RNA of the biological sample is used in the polymerase chain reaction. The nucleic acid may be double stranded or single stranded. Various methods using polymerase chain reaction are known in the art, including reverse transcription RNA, quantitative PCR, and multiplex PCR.

In general, polymerase chain reactions rely on cycling through a series of steps including annealing and extension/elongation. A pair of oligonucleotides (e.g., primers) has sufficient complementary to a desired nucleic acid (e.g. a biomarker) if present in the sample such that the primer anneals (hybridizes) the desired nucleic acid, under appropriate annealing conditions (e.g., annealing temperature). The reaction proceeds to an extension/elongation step in which a polymerase synthesizes a complementary nucleic acid strand. The double stranded nucleic acid product is denatured and another cycle of the reaction is initiated.

In some embodiments, the polymerase chain reaction involves different temperature settings for each of the steps of the cycle. In some embodiments, the polymerase chain reaction is performed at a single temperature (e.g., isothermal reaction).

Polymerase chain reactions, as described above, allow for the selective amplification of nucleic acids based on selection of the oligonucleotide primers. In some embodiments, nucleic acids corresponding to the RNA biomarker set are selectively amplified and subsequently detected using any method known in the art. In some embodiments, the amplified product may be detected using hybridization methods. Alternatively or in addition, the amplified product may be detected by one or more modifications introduced during the polymerase chain reaction. In some embodiments, a dye, fluorophore or other indicator agent is intercalated into the nucleic acid during the polymerase chain reaction. In some embodiments, one or more of the nucleic acid primers may comprise a tag (e.g., a nucleic acid tag) that may be detected.

In some embodiments, a RNA biomarker is measured using methods involving hybridization, for example with an oligonucleotide that is complementary (partially or completely) to the RNA biomarker. In some embodiments, the hybridization method is performed on the biological sample to detect the RNA biomarker or on a composition (e.g., PCR reaction) comprising an amplified product (e.g., amplified RNA biomarker or cDNA corresponding to the RNA biomarker). In some embodiments, the hybridization involves contacting the sample with an oligonucleotide (e.g., a probe) that specifically binds to the biomarker. Examples of hybridization methods include, without limitation, Southern blotting, Northern blotting, and microarray methods. As described herein, in some embodiments, the oligonucleotide may be conjugated to a label for detection and/or immobilized on a support member.

Selection of appropriate buffers, polymerases, hybridization conditions will be evident to one of ordinary skill in the art and optimization may involve routine experimentation.

In some embodiments, the biomarker is measured using nucleic acid sequencing. For example, the abundance of a particular nucleic acid sequence (e.g. of a biomarker) in a sample can be compared to the abundance of the same nucleic acid sequence in another sequence (e.g., whole transcriptome sequencing, RNASeq). Such comparison can be performed, for example, by comparing the number of reads of a particular sequence between samples.

In general, nucleic acid sequencing may be performed using any method known in the art and selection of an appropriate method will be evident to one of ordinary skill in the art. For example, nucleic acid may be sequenced using Sanger sequencing or high-throughput sequencing methods.

In some embodiments, the biological sample is subjected to a RNA extraction process to isolate the RNA present in the sample (e.g., prior to measuring the biomarker). Such RNA extraction processes are well known in the art. Examples of RNA extraction processes include commercially available kits and phenol-chloroform extraction. In some embodiments, the RNA extracted from the biological sample is subjected to in vitro translation, thereby producing proteins encoded by the RNA, including proteins encoded by a RNA biomarker, if present. In some embodiments, the biological sample or the RNA extracted from the biological sample is subjected to reverse transcription, thereby producing cDNA corresponding to the RNA, including the RNA biomarkers, if present.

In some embodiments, the biomarker is measured using an immunoassay. In some embodiments, a biological sample is contacted with a binding agent, such as nucleic acid-binding protein, that binds to a RNA biomarker. An immunoassay may then be performed to detect the binding agent, as an indirect measure of the amount of the biomarker in the sample. Examples of immunoassays include, without limitation immunoblotting assays (Western blots), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a biomarker provided herein, for example by detecting a binding agent that binds to the biomarker, will be apparent to those of skill in the art. It will be apparent to those of skill in the art that this disclosure is not limited to immunoassays, however, and that detection assays that rely on a chromogenic substrate can also be useful for the detection and/or quantification of contact system biomarkers as provided herein.

ELISAs are known in the art (see, e.g., Crowther, John R (2009). "The ELISA Guidebook." 2nd ed. Humana Press and Lequin R (2005). "Enzyme immunoassay (EIA)/enzyme-linked immunosorbent assay (ELISA)". *Clin. Chem.* 51 (12): 2415-8) and exemplary ELISAs are described herein. Kits for performing ELISAs are also known in the art and commercially available (see, e.g., ELISA kits from Life Technologies and BD Biosciences).

The immunoassays described herein may be in the format of a sandwich ELISA, in which a first binding agent that specifically binds a binding agent (e.g., a nucleic acid-binding protein that binds to the RNA biomarker) is immobilized on a support member. The support member can then be incubated with a biological sample as described herein for a suitable period of time under conditions that allow for the formation of complex between the binding agent and the biomarker in the sample. Such a complex can then be detected using a detection agent that binds the biomarker, the binding agent-biomarker complex, or the binding agent. The detection agent can be conjugated to a label, as described herein, which can release a signal directly or indirectly. The intensity of the signal represents the level of the RNA biomarker in the sample. In some embodiments, the detection agent is detected and its level represents the level of the RNA biomarker in the sample.

Any binding agent that specifically binds to a desired nucleic acid may be used in the methods and kits described herein to measure the level of a RNA biomarker in a biological sample. In some embodiments, the binding agent is an antibody that specifically binds to a desired nucleic acid. In some embodiments, a sample may be contacted, simultaneously or sequentially, with more than one binding agent that bind different RNAs (e.g., multiplexed analysis, for example the SOMAScan™ assay (SOMALogic)). The biological sample is contacted with a binding agent under appropriate conditions. In general, the term "contact" refers to an exposure of the binding agent with the biological sample or agent for a suitable period sufficient for the formation of complexes between the agent and the RNA in the sample, if any. In some embodiments, the contacting is performed by capillary action in which a biological sample or agent is moved across a surface of the support membrane.

In some embodiments, the immunoassays may be performed on low-throughput platforms, including in single immunoassay format. For example, a low throughput platform may be used to measure the presence and amount of a nucleic acid in biological samples (e.g., biological tissues, tissue extracts) for diagnostic methods, monitoring of disease and/or treatment progression, and/or predicting whether a disease or disorder may benefit from a particular treatment.

In some embodiments, it may be necessary to immobilize a binding agent to the support member. Methods for immobilizing a binding agent will depend on factors such as the nature of the binding agent and the material of the support member and may require particular buffers. Such methods will be evident to one of ordinary skill in the art. For example, the biomarker set in a biological sample as described herein may be measured using any of the kits and/or detecting devices which are also described herein.

As used herein, the terms "measuring" or "measurement," or alternatively "detecting" or "detection," mean assessing the presence, absence, quantity or amount (which can be an effective amount) of a substance within a sample, including the derivation of qualitative or quantitative concentration levels of such substances, or otherwise evaluating the values or categorization of a subject.

Assays, e.g., Southern or Northern blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

In any of the methods described herein, the level of a RNA of a biomarker set can be compared to the level of the RNA in a control sample or a reference sample.

The methods and kits described herein, involving any of the RNA biomarker set also described herein, can be applied for the evaluation of a disease associated with the contact activation system, such as those described herein.

(ii) Diagnostic and/or Prognostic Applications

The levels of RNAs presented in Table 1 detected in samples from subjects can be used as reliable biomarkers for diagnosing diseases associated with the contact activation system (e.g., HAE), monitoring the progress of such a disease, assessing the efficacy of a treatment for the disease, identifying patients suitable for a particular treatment, and/ or predicting disease attack in a subject.

Accordingly, described herein are diagnostic and prognostic methods for a disease associated with the contact activation system based on the level of a biomarker set in a biological sample obtained from a subject. In some embodiments, the level of the biomarker, as measured using any of the methods described herein, can be relied on to evaluate whether a subject (e.g., a human patient) from whom the biological sample is obtained, has or is at risk for a disease associated with the contact activation system, such as a disease associated with plasma kallikrein, e.g., HAE or autoimmune disease such as RA, UC, and Crohn's disease.

In some embodiments, the level of the biomarker can then be compared with a reference sample or a control sample to determine a value indicating the amount of the RNA in the sample. In some embodiments, a value for a biomarker is obtained by comparing the level of a RNA in a sample to the level of another RNA (e.g., an internal control or internal standard) in the sample. Such a biomarker value may be a normalized value over the internal control or internal standard. The value of the biomarker can be compared to a reference value to determine whether the subject has or is at risk for the disease associated with the contact system. The reference value may represent the level of the corresponding biomarker in subjects (e.g., human subjects) free of the target disease. In some embodiments, if the level or value of the biomarker is higher than a reference level or value, the subject can be identified as having or at risk for a disease associated with the contact activation system. In some embodiments, if the level or value of the biomarker is lower than a reference level or value, the subject can be identified as having or at risk for a disease associated with the contact activation system.

In some embodiments, the level of the biomarker can be compared to a predetermined threshold for the RNA biomarker, a deviation from which may indicate the subject has a disease associated with the contact system. The predetermined threshold may represent the value of the biomarker that distinguishes the level of the biomarker in patients having the target disease from the level of the biomarker in patients free of the target disease.

In some embodiments, the biomarker set includes more than one RNA biomarkers that are differentially present (elevated and/or reduced) in a subject having or being at risk of having the disease as relative to healthy subjects. In some examples, the biomarker set includes at least one RNA biomarker that has an elevated level in a subject having or being at risk of having the disease and at least one RNA biomarker that has a reduced level in the subject having or at risk for the disease. Examples of the "elevated" and "reduced" RNA biomarkers are listed in Table 1. In some embodiments, the biomarker set includes more than one RNA, for each of which an elevated level indicates the subject has or is at risk of having the disease. In some embodiments, the biomarker set includes more than one RNA, for each of which a reduced level indicates the subject has or is at risk of having the disease.

In some embodiments, the control sample or reference sample is a biological sample obtained from a healthy individual. In some embodiments, the control sample or reference sample contains a known amount of the RNA to be assessed. In some embodiments, the control sample or reference sample is a biological sample obtained from a control subject.

As used herein, a control subject may be a healthy subject or healthy individual, that is apparently free of the target disease (e.g., a disease associated with the contact system) at the time the level of the RNA(s) is measured or has no history of the disease. The term "control subject" encompasses an individual subject or a group of subjects having similar characteristics, for example, a group of healthy subjects having certain features matching those of the candidate subject, e.g., age, gender, ethnic group, etc. In some embodiments, the level of a biomarker in a control subject is used to establish a reference value (e.g., the average level of the biomarker in a control subject, which includes a group of subjects) that may be compared to the level of the biomarker in a candidate or test subject.

The control level refers to the level of a RNA biomarker set as described herein in a control subject. The control level can be a predetermined level or threshold. Such a predetermined level can represent the level of the RNA in a population of subjects that do not have or are not at risk for the target disease (e.g., the average level in the population of healthy subjects). It can also represent the level of the RNA in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the RNA in a control population.

The control level as described herein can be determined by routine technology. In some examples, the control level can be obtained by performing a conventional method (e.g., the same assay for obtaining the level of the RNA a test sample as described herein) on a control sample as also described herein. In other examples, levels of the RNA can be obtained from members of a control population and the results can be analyzed by, e.g., a computational program, to obtain the control level (a predetermined level) that represents the level of the RNA in the control population.

By comparing the level of a biomarker in a sample obtained from a candidate subject to the reference value as described herein, it can be determined as to whether the candidate subject has or is at risk for a disease associated with the contact system (e.g., HAE). For example, if the level of biomarker(s) in a sample of the candidate subject deviates from the reference value (e.g., increased as compared to the reference value), the candidate subject might be identified as having or at risk for the disease. When the reference value represents the value range of the level of the biomarker in a population of subjects that have the target disease, the value of biomarker in a sample of a candidate falling in the range indicates that the candidate subject has or is at risk for the target disease.

As used herein, "an elevated level" or "a level above a reference value" means that the level of the biomarker is higher than a reference value, such as a pre-determined threshold of a level the biomarker in a control sample. Control levels are described in detail herein. An elevated level of a biomarker includes a level of the biomarker that is, for example, 1%, 5%, 10%, 20%, 30%, 40%, 50%, 60%, 70%, 80%, 90%, 100%, 150%, 200%, 300%, 400%, 500% or more above a reference value. In some embodiments, the level of the biomarker in the test sample is at least 1.1., 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or higher than the level of the biomarker in a reference sample.

As used herein, "a decreased level" or "a level below a reference value" means that the level of the biomarker is lower than a reference value, such as a pre-determined threshold of the biomarker in a control sample. Control levels are described in detail herein. A decreased level of the biomarker includes a level of the biomarker that is, for example, 1%, 5%, 10%, 20%, 30%, 40%, 50%, 60%, 70%, 80%, 90%, 100%, 150%, 200%, 300%, 400%, 500% or more lower than a reference value. In some embodiments, the level of the biomarker in the test sample is at least 1.1., 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or lower than the level of the biomarker in a reference sample.

In some embodiments, the candidate subject is a human patient having a symptom of a disease associated with the contact activation system, such as a pKal-mediated disorder, e.g., HAE or an autoimmune disease such as RA, UC, and Crohn's disease. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an antihistamine therapy, a corticosteroid therapy, or both.

A subject identified in the methods described herein may be subject to a suitable treatment, such as treatment with a pKal inhibitor, as described herein.

The assay methods and kits described herein also can be applied for evaluation of the efficacy of a treatment for a disease associated with the contact system, such as those described herein, given the correlation between the level of the biomarkers and such diseases. For examples, multiple biological samples (e.g., blood or plasma samples) can be collected from a subject to whom a treatment is performed either before and after the treatment or during the course of the treatment. The levels of a biomarker can be measured by any of the assay methods as described herein and values (e.g., amounts) of a biomarker can be determined accordingly. For example, if an elevated level of a biomarker indicates that a subject has a target disease and the level of the biomarker decreases after the treatment or over the course of the treatment (the level of the biomarker in a later collected sample as compared to that in an earlier collected sample), it indicates that the treatment is effective. As another example, if a reduced level of a biomarker indicates that a subject has a target disease and the level of the biomarker increases after the treatment or over the course of the treatment (the level of the biomarker in a later collected sample as compared to that in an earlier collected sample), it indicates that the treatment is effective. In some examples, the treatment involves an effective amount of a therapeutic agent, such as a plasma kallikrein inhibitor, a bradykinin B2 receptor antagonist, or a C1 esterase inhibitor (C1-INH). Examples of the therapeutic agents include, but not limited to, lanadelumab, ecallantide, icatibant, and human plasma-derived C1-INH.

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a biomarker or biomarker set can also be relied on to identify that a disorder is associated with the contact system or that the disorder may be treatable, for example by a pKal inhibitor. To practice this method, the level of a biomarker in a sample collected from a subject (e.g., a blood sample or a plasma sample) having a target disease can be measured by a suitable method, e.g., those described herein such as mass spectrometry, chromatography, immunoassays. If the level of the biomarker deviates from the reference value (e.g., elevated or decreased), it indicates that a pKal inhibitor may be effective in treating the disease. If the disease is identified as being susceptible (can be treated by) to a pKal inhibitor, the method can further comprise administering to the subject having the disease an effective amount of a pKal inhibitor, such as an anti-pKal antibody or an inhibitory peptide (e.g., lanadelumab, ecallantide, etc.); a bradykinin 2 receptor inhibitor (e.g., icatibant); and/or a C1-INH (e.g. human plasma-derived C1-INH).

Also within the scope of the present disclosure are methods of evaluating the severity of a disease associated with the contact system or the disease state. For example, as described herein, HAE may be in the quiescent state (basal state), during which the subject does not experience symptoms of the disease. HAE attacks are typically recurrent episodes in which the subject may experience pain and swelling, for example in the hands, feet, face, gastrointestinal tract, genitals, and larynx (throat) that can last from two to five days. In some embodiments, the level of one or more biomarker is indicative of whether the subject will experience, is experiencing, or will soon experience an HAE attack. In some embodiments, the methods involve comparing the level of a biomarker in a sample obtained from a subjecting having HAE to the level of the biomarker in a sample from the same subject, for example a sample obtained from the same subject at basal state or a sample obtained from the same subject during a HAE attack.

Other aspects of the disclosure provide methods for assessing the risk of disease attack (e.g., HAE attack). As described herein, HAE attacks are typically recurrent episodes during which the subject may experience symptoms such as pain and swelling. In some embodiments, the level of one or more biomarker is indicative of whether the subject is at risk of having an HAE attack. In some embodiments, the methods involve comparing the level of a biomarker in a sample obtained from a subjecting having HAE to the level of the biomarker in a sample from the same subject, for example a sample obtained from the same subject at basal state or a sample obtained from the same subject during a HAE attack. For example, the level of the biomarker in another sample from the subject may indicated that the subject is an increase (or a decrease) in the level of a biomarker associated with an HAE attack as compared to at risk of having an HAE attack.

In some embodiments, the methods involve comparing the level of a biomarker in a sample obtained from a subjecting having HAE to the level of the biomarker in a control or reference sample. In some embodiments, the level of the biomarker in the control or reference sample represents the level of the biomarker that indicates a HAE attack state. For example, a level of the biomarker in a sample obtained from a subjecting having HAE that is similar to the level of the biomarker in a reference that represents an HAE attack state, may indicate that the subject is at risk of having a HAE attack. In some embodiments, the level of the biomarker in the control or reference sample represents the level of the biomarker that indicates HAE in the basal state. For example, a level of the biomarker in a sample obtained from a subjecting having HAE that deviates (is elevated or reduced) to the level of the biomarker in a reference that represents a HAE in the basal state, may indicate that the subject is at risk of having a HAE attack.

(iii) Non-Clinical Applications

Further, levels of any of the biomarker set described herein may be used for research purposes. Although many diseases associated with the contact activation system have been identified, it is possible that other diseases are mediated by similar mechanisms or involve similar components. In some embodiments, the methods described herein may be used to identify a disease as being associated with the contact activation system or with components of the contact activation system. In some embodiments, the methods described herein may be used to study mechanisms (e.g., the discovery of novel biological pathways or processes involved in disease development) or progression of a disease.

In some embodiments, the levels of biomarker sets, as described herein, may be relied on in the development of new therapeutics for a disease associated with the contact activation system. For example, the levels of a biomarker set may be measured in samples obtained from a subject having been administered a new therapy (e.g., a clinical trial). In some embodiments, the level of the biomarker set may indicate the efficacy of the new therapeutic or the progression of the disease in the subject prior to, during, or after the new therapy.

Kits and Detecting Devices for Measuring RNA Biomarker Sets

The present disclosure also provides kits and detecting devices for use in measuring the level of a biomarker set as described herein. Such a kit or detecting device can comprise binding agents that specifically bind to the RNA biomarkers, such as those listed in Table 1. For example, such a kit or detecting device may comprise at least two binding agents that are specific to two different RNA biomarkers selected from Table 1. In some instances, the kit or detecting device comprises binding agents specific to all members of the RNA biomarker set described herein.

In some embodiments, the binding agent is an oligonucleotide, as described herein, which is complementary to a RNA biomarker. In some embodiments, the binding agent comprises a pair of oligonucleotides (e.g., a primer pair) each of which binds (hybridizes) to a specific nucleotide sequence in the RNA biomarker. In some embodiments, the pair of oligonucleotides hybridizes to the RNA biomarker and allow for the amplification of the RNA biomarker, when subjected to methods such as polymerase chain reaction. In some embodiments, the amplified product may be directly detected, for example by detecting a dye, fluorophore or other indicator agent that is intercalated into the nucleic acid during the polymerase chain reaction. In some embodiments, at least one of the oligonucleotides is conjugated to a label, which can be detected.

In some embodiments, the RNA biomarker is measured using a nucleic acid hybridization method. In some embodiments, the binding agent is an oligonucleotide that is complementary to a RNA biomarker and hybridizes to the RNA biomarker, if present in a sample (e.g., a biological sample or a sample from polymerase chain reaction). In some embodiments, the oligonucleotide is conjugated to a label, such as any of the labels described herein, which can be detected. Non-limiting examples of hybridization methods, as described herein, include Northern blotting, Southern blotting, and microarrays.

In some embodiments, one or more of the binding agents is a nucleic-acid binding protein that specifically binds to a RNA of the biomarker set. In some embodiments, the binding agent is directly detected or may be conjugated to a tag that can be identified and, directly or indirectly.

In some embodiments, the kit or device further includes a support member, as described herein. In the kit or detecting device, one or more of the binding agents may be immobilized on a support member, e.g., a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The included instructions can comprise a description of how to use the components contained in the kit for measuring the level of RNAs of RNA biomarker set in a biological sample collected from a subject, such as a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of RNAs of a biomarker set. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Treatment of Diseases Associated with Contact Activation System

A subject at risk for or suffering from a disease associated with the contact activation system, as identified using the methods described herein, may be treated with any appropriate therapeutic agent. In some embodiments, provided methods include selecting a treatment for a subject based on the output of the described method, e.g., measuring the level of a biomarker set.

In some embodiments, the methods described herein provide methods of identifying a subject as a candidate for preventative (prophylactic) treatment. As used herein, a "preventative" treatment includes any therapy or treatment regimen that aims to prevent or reduce the incidence of a disease (e.g., HAE attack). In some embodiments, the methods further comprise administering a preventative treatment to the subject. Any of the therapeutic agents described herein (e.g., pKal inhibitors, such as lanadelumab). In some embodiments, the level of a RNA biomarker set in a sample obtained from a subject indicates that the patient has or is at risk of having HAE (e.g., by comparing the level of the RNA biomarker to the level in a reference or control sample). Any subject having or at risk of having HAE may be administered a prophylactic treatment. Selection of an appropriate therapeutic agent and administration regimen for a preventative treatment will be evident to one of ordinary skill in the art.

In some embodiments, the method comprises one or both of selecting or administering a therapeutic agent, e.g., a kallikrein inhibitor, a bradykinin B2 receptor inhibitor, and/or a C1 esterase inhibitor, for administration to the subject based on the output of the assay, e.g., biomarker detection.

In some embodiments, the therapeutic agent is administered one or more times to the subject. In some embodiments, a plasma kallikrein inhibitor is administered to a subject. In some embodiments, kallikrein inhibitor is a peptide, a small molecule inhibitor, a kallikrein antibody, or a fragment thereof. In some embodiments, an antagonist of bradykinin B2 receptor is administered to a subject. In some embodiments, a C1-INH is administered to a subject.

The therapeutic agent, e.g., kallikrein inhibitor, bradykinin B2 receptor inhibitor, and/or C1-INH, may be administered along with another therapy as part of a combination therapy for treatment of the disease or condition that involves the contact activation system. Combination therapy, e.g., with one or more of a kallikrein inhibitor, bradykinin B2 receptor antagonist, or C, 1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Therapeutic Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding agent such as a plasma kallikrein inhibitor is administered to a subject at risk or suffering from a disease associated with the contact activation system.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., *Protein Engineering* (1990) 3(7):591-598; Hynes et al., *Biochemistry* (1990) 29:10018-10022) are known. At least eighty one Kunitz domain sequences are known. Known human homologues include three Kunitz domains of LACI also known as tissue factor pathway inhibitor (TFPI) (Wun et al., *J. Biol. Chem.* (1988) 263(13):6001-6004; Girard et al., *Nature* (1989) 338:518-20; Novotny et al, *J. Biol. Chem.* (1989) 264(31):18832-18837) two Kunitz domains of Inter-α-Trypsin Inhibitor, APP-I (Kido et al. *J. Biol. Chem.* (1988) 263(34):18104-18107), a Kunitz domain from collagen, three Kunitz domains of TFPI-2 (Sprecher et al., PNAS USA (1994) 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 2004-0152633. LACI is a human serum phosphoglycoprotein with a molecular weight of 39 kDa (amino acid sequence in Table 2) containing three Kunitz domains.

A4_MOUSE (P12023), A4_RAT (P08592), A4_SAISC (Q95241),
AMBP_PLEPL (P36992), APP2_HUMAN (Q06481), APP2_RAT (P15943),
AXP1_ANTAF (P81547), AXP2_ANTAF (P81548), BPT1_BOVIN (P00974),
BPT2_BOVIN (P04815), CA17_HUMAN (Q02388), CA36_CHICK (P15989),
CA36_HUMAN (P12111), CRPT_BOOMI (P81162), ELAC_MACEU (O62845),
ELAC_TRIVU (Q29143), EPPI_HUMAN (O95925), EPPI_MOUSE (Q9DA01),
HTIB_MANSE (P26227), IBP_CARCR (P00993), IBPC_BOVIN (P00976),
IBPI_TACTR (P16044), IBPS_BOVIN (P00975), ICS3_BOMMO (P07481),
IMAP_DROFU (P11424), IP52_ANESU (P10280), ISC1_BOMMO (P10831),
ISC2_BOMMO (P10832), ISH1_STOHE (P31713), ISH2_STOHE (P81129),
ISIK_HELPO (P00994), ISP2_GALME (P81906), IVB1_BUNFA (P25660),
IVB1_BUNMU (P00987), IVB1_VIPAA (P00991), IVB2_BUNMU (P00989),
IVB2_DABRU (P00990), IVB2_HEMHA (P00985), IVB2_NAJNI (P00986),
IVB3_VIPAA (P00992), IVBB_DENPO (P00983), IVBC_NAJNA (P19859),
IVBC_OPHHA (P82966), IVBE_DENPO (P00984), IVBI_DENAN (P00980),
IVBI_DENPO (P00979), IVBK_DENAN (P00982), IVBK_DENPO (P00981),
IVBT_ERIMA (P24541), IVBT_NAJNA (P20229), MCPI_MELCP (P82968),

TABLE 2

Exemplary Natural Kunitz Domains

```
LACI          1   MIYTMKKVHA LWASVCLLLN LAPAPLNAds eedeehtiit dtelpplklM
(SEQ ID      51   HSFCAFKADD GPCKAIMKRF FFNIFTRQCE EFIYGGCEGN QNRFESLEEC
NO: 1)      101   KKMCTRDnan riikttlqqe kpdfCfleed pgiCrgyitr yfynnqtkqC
            151   erfkyggClg nmnnfetlee CkniCedgpn gfqvdnygtq lnavnnsltp
            201   qstkvpslfe fhgpswCltp adrglCrane nrfyynsvig kCrpfkysgC
            251   ggnennftsk qeClraCkkg fiqriskggl iktkrkrkkq rvkiayeeif
            301   vknm
            The signal sequence (1-28) is uppercase and underscored
            LACI-K1 (50-107) is uppercase
            LACI-K2 (121-178) is underscored
            LACI-K3 (211-270) is bold BPTI                       1          2          3          4          5
(SEQ ID      12345678901234567890123456789012345678901234567890123456 78
NO: 2)       RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (*J. Biol. Chem.* (1988) 263(13):6001-6004). Girard et al. (*Nature* (1989) 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins Containing Exemplary Kunitz Domains Include the Following, with SWISS-PROT Accession Numbers in parentheses:

A4_HUMAN (P05067), A4_MACFA (P53601), A4_MACMU (P29216),

SBPI_SARBU (P26228), SPT3_HUMAN (P49223), TKD1_BOVIN (Q28201),
TKD1_SHEEP (Q29428), TXCA_DENAN (P81658), UPTI_PIG (Q29100),
AMBP_BOVIN (P00978), AMBP_HUMAN (P02760), AMBP_MERUN (Q62577),
AMBP_MESAU (Q60559), AMBP_MOUSE (Q07456), AMBP_PIG (P04366),
AMBP_RAT (Q64240), IATR_HORSE (P04365), IATR_SHEEP (P13371),
SPT1_HUMAN (O43278), SPT1_MOUSE (Q9R097), SPT2_HUMAN (O43291),
SPT2_MOUSE (Q9WU03), TFP2_HUMAN (P48307), TFP2_MOUSE (O35536),

TFPI_HUMAN (P10646), TFPI_MACMU (Q28864), TFPI_MOUSE (O54819),
TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda MD), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. Proteins (1997) 28(3):405-420 and a detailed description of HMMs can be found, for example, in Gribskov et al. *Meth. Enzymol.* (1990) 183:146-159; Gribskov et al. *Proc. Natl. Acad. Sci. USA* (1987) 84:4355-4358; Krogh et al. *J. Mol. Biol.* (1994) 235:1501-1531; and Stultz et al. *Protein Sci.* (1993) 2:305-314. The SMART database (Simple Modular Architecture Research Tool, EMBL, Heidelberg, DE) of HMMs as described in Schultz et al. *Proc. Natl. Acad. Sci. USA* (1998) 95:5857 and Schultz et al. *Nucl. Acids Res* (2000) 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains (Corpet et al. *Nucl. Acids Res*. (1999) 27:263-267). Current versions of ProDom are built using recursive PSI-BLAST searches (Altschul et al. *Nucleic Acids Res*. (1997) 25:3389-3402; Gouzy et al. *Computers and Chemistry* (1999) 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. (2002) 30:235-238.

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., Nature (1989) 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, the plasma kallikrein inhibitor binds to the active form of plasma kallikrein. In some embodiments, the plasma kallikrein inhibitor, binds to and inhibits plasma kallikrein, e.g., human plasma kallikrein and/or murine kallikrein. Exemplary polypeptide plasma kallikrein agents are disclosed in U.S. Pat. Nos. 5,795,865, 5,994,125, 6,057,287, 6,333,402, 7,628,983, and 8,283,321, 7,064,107, 7,276,480, 7,851,442, 8,124,586, 7,811,991, and U.S. Publication No. 20110086801, the entire contents of each of which is incorporated herein by reference. In some embodiments, the plasma kallikrein inhibitor is an inhibitory polypeptide or peptide. In some embodiments, the inhibitory peptide is ecallantide (also referred to as DX-88 or KALBITOR®; SEQ ID NO:3). In some embodiments, the kallikrein inhibitor comprises or consists of an about 58-amino acid sequence of amino acids 3-60 of SEQ ID NO:3 or the DX-88 polypeptide having the 60-amino acid sequence of SEQ ID NO:3.

Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:3).

Plasma kallikrein inhibitor can be full-length antibodies (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein inhibitor can be recombinant proteins such as humanized, CDR grafted, chimeric, deimmunized, or in vitro generated antibodies, and may optionally include constant regions derived from human germline immunoglobulin sequences. In one embodiment, the plasma kallikrein inhibitor is a monoclonal antibody.

Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930 or lanadelumab), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04. In some embodiments, the plasma kallikrein binding protein is lanadelumab. See US Publication No. 20110200611 and US Publication No. 20120201756, which are incorporated by reference herein.

An example of a plasma kallikrein inhibitory antibody is lanadelumab. The amino acid sequences of the heavy chain and light chain variable regions of lanadelumab are provided below with the CDR regions identified in boldface and underlined.

```
Lanadelumab heavy chain variable region sequence
                                        (SEQ ID NO: 4)
EVQLLESGGG LVQPGGSLRL SCAASGFTFS HYIMMWVRQA
PGKGLEWVSG IYSSGGITVY ADSVKGRFTI SRDNSKNTLY
LQMNSLRAED TAVYYCAYRR IGVPRRDEFD IWGQGTMVTV SS Lanadelumab light chain variable region sequence
                                        (SEQ ID NO: 5)
DIQMTQSPS TLSASVGDRV TITCRASQSI SSWLAWYQQK
PGKAPKLLIY KASTLESGVP SRFSGSGSGT EFTLTISSLQ
PDDFATYYCQ QYNTYWTFGQ GTKVEI
```

In some embodiments, a plasma kallikrein inhibitor can have about 85%, 90%, 91%, 92%, 93%, 94%, 95%, 96%, 97%, 98%, 99% or higher sequence identity to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the constant region (e.g., CH1, CH2, CH3, and/or CL1) to a plasma kallikrein inhibitor described herein.

In some aspects, a small molecule binds and inhibits the active form of plasma kallikrein.

Bradykinin B2 Receptor Inhibitors

In some embodiments, a bradykinin B2 receptor inhibitor (e.g., antagonist) is administered to a subject. Exemplary bradykinin B2 receptor antagonists include icatibant (Firazyr®), which is a peptidomimetic drug containing 10 amino acids which block binding of native bradykinin to the bradykinin B2 receptor.

C1-INH Replacement Agents

In some embodiment, a C1 esterase inhibitor (C1-INH), such as a replacement C1-INH agent is administered to a subject. Exemplary C1-INH replacement agents are publicly available and include, for example, human plasma-derived C1-INH, e.g. Berinert® and CINRYZE®.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Identification of RNA Molecules Differentially Present in Samples from HAE Patients Compared to Healthy Individuals To investigate novel RNA biomarkers of hereditary angioedema, an analysis was performed comparing the circulating small RNAs present in plasma samples obtained from patients with HAE to samples obtained from healthy individuals. Circulating citrated plasma was collected from healthy individuals (n=3) and patients having HAE during disease quiescence ("basal," N=19) and during an edematous attack ("attack," N=20). RNA was extracted from the plasma samples. Library fragments of 128-158 nucleotides were sequences using a HiSeq 2500 sequencing system (Illumina). The reads were de-multiplexed, adaptor sequences were removed and unique sequences with >5 reads were created. Using Bowtie2, a sequence alignment tool (bowtie-bio.sourceforge.net/bowtie2/manual.shtml), non-redundant sequences were aligned to a reference genome (hg19), and sequences with perfect-match and 1 nucleotide mismatch alignments were further aligned with cDNA, non-coding RNA, miRNA and piRNA databases. The RNASeq data identified 1,811 detectable human RNA transcripts and 457 human microRNAs (≥10 reads in ≥25% of samples). The abundance of each of the detected RNAs were compared between the samples from healthy individuals and patients having HAE. RNA transcripts encoding certain mitochondrial proteins were found to be significantly elevated in samples from HAE patients as compared to samples from healthy individuals (FIG. 1). Additionally, the RNASeq analysis identified 24 microRNAs that were differentially expressed in samples from HAE patients as compared to samples from healthy individuals. The identified RNA transcripts and microRNAs were validated using RT-qPCR on independent samples obtained from healthy individuals (N=20), patients having HAE during disease quiescence (N=34) and during an edematous attack (N=18).

As shown in FIG. 1, RNA transcripts of mitochondria-encoded transcripts for Mitochondrial Encoded NADH: Ubiquinnone Oxidoreductase Core Subunit 3 (MT-ND3) and Mitochondrial Encoded Cytochrome C Oxidase III were higher in samples from patients having HAE (during attack or quiescence) as compared to in samples from healthy individuals in the initial RNASeq as well as by RT-qPCR analysis. These results indicated that these RNA can be used as biomarkers to distinguish between samples from patients with HAE from healthy individuals.

Figure 2:
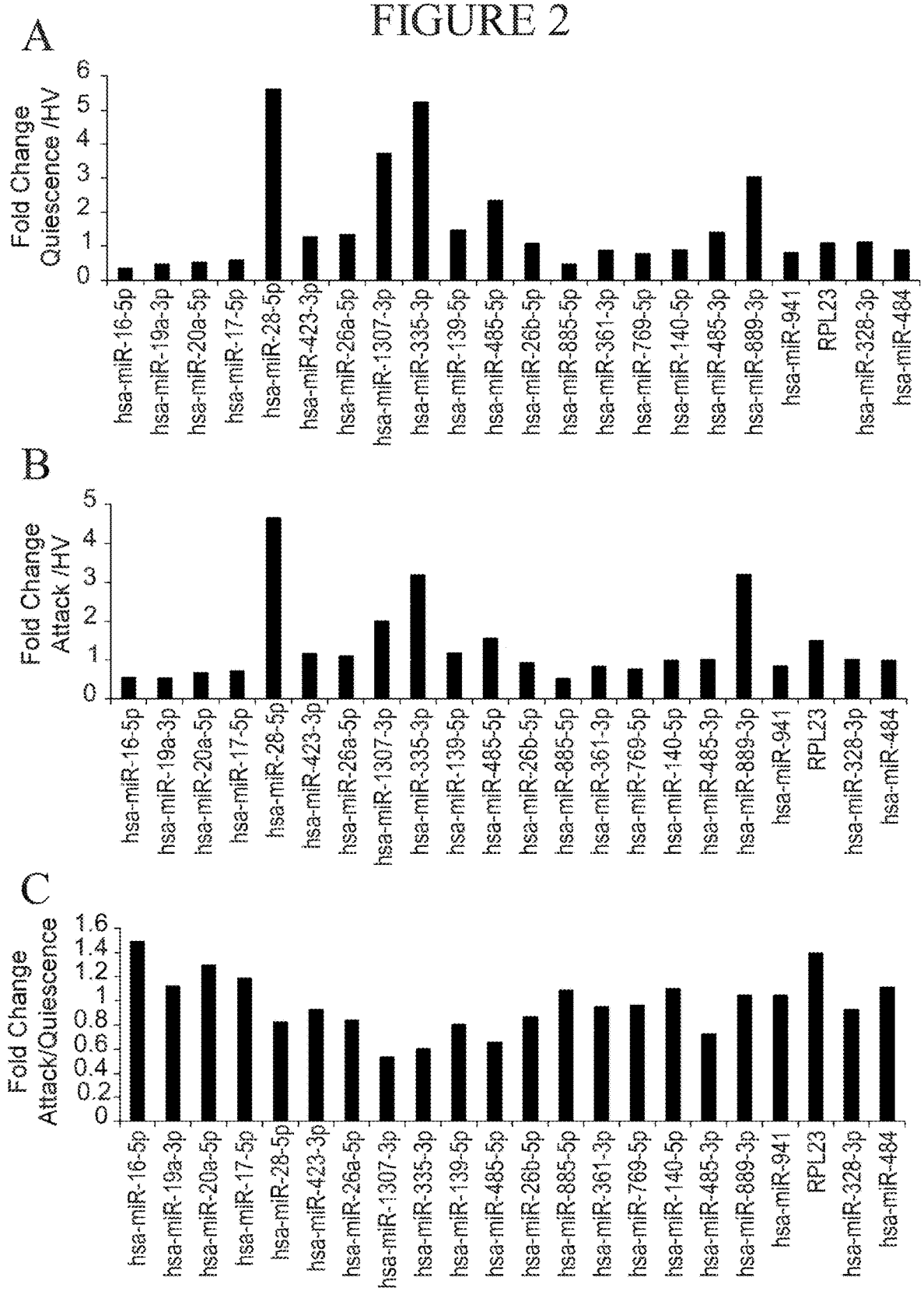
FIG. 2 presents graphs showing levels of selected microRNA levels in plasma samples obtained from healthy individuals and HAE patients. A: fold change of RNA transcript in quiescence (HAE in basal state) compared to healthy individual ("HV"). B: fold change of RNA transcript in HAE during attack compared to healthy individual ("HV"). C: fold change of RNA transcript in HAE during attack compared to quiescence (HAE in basal state).

As shown in FIG. 2, panels A and B, several microRNAs were found to be differentially present in samples obtained from HAE patients and healthy individuals. For example, hsa-miR-423-3p, hsa-miR-1307-3p, hsa-miR-355-3p, and hsa-miR-485-5p were elevated in samples from HAE patients. Several microRNAs were also found at reduced levels in samples from HAE patients, including hsa-miR-16-5p, hsa-miR-19a-3p, hsa-miR-20a-5p, hsa-miR-17-5p, and hsa-miR-885-5p. Finally, the analysis also identified several microRNAs that were reduced in samples from HAE patients during an attack as compared to at basal state, for example, has-miR-1307-3p, hsa-miR-335-3p, and hsa-miR-485-5p (FIG. 2, panel C).

Any of the RNAs identified herein (e.g., RNAs having a significant fold change between HAE patients and healthy individuals), may be used as a biomarker (individually or in combination (biomarker set)) for diseases associated with the contact activation system, for example in methods for identifying patients who are at risk of a disease associated with the contact activation system (e.g., HAE), selecting a candidate for treatment, monitoring disease progression or disease state, assessing the efficacy of a treatment against a disease, determining a course of treatment, identifying whether a disease or disorder is associated with the contact activation system, and/or for research purposes, including, e.g., studying the mechanism of a disease, which may be relied upon for the development of new therapies.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for analyzing a sample, comprising:
  (i) providing a biological sample obtained from a subject having, suspected of having, or being at risk for hereditary angioedema (HAE);
  (ii) measuring the level of a RNA biomarker set, wherein the RNA biomarker set comprises a messenger RNA encoding mitochondrially-encoded cytochrome C oxidase III (MT-CO3);
  (iii) identifying the subject as a subject having HAE based on the level of the RNA biomarker set, an increase of the level of MT-CO3 of the subject from that of a control subject being indicative of the subject having HAE; and
  (iv) administering to the subject identified as having HAE in step (iii) an effective amount of a therapeutic agent for treating HAE;
  wherein the therapeutic agent is a plasma kallikrein (pKal) inhibitor, a bradykinin 2 receptor (B2R) inhibitor, and/or a C1 esterase inhibitor.

2. The method of claim 1, wherein the biomarker set consists of 2-10 RNA biomarkers.

3. The method of claim 1, wherein the biological sample is a serum sample or a plasma sample.

4. The method of claim 1, wherein the HAE is type I HAE or type II HAE.

5. The method of claim 1, wherein the RNA biomarker set further comprises a microRNA.

6. The method of claim 1, wherein step (ii) involves polymerase chain reaction and/or nucleic acid hybridization.

7. The method of claim 1, wherein the subject is a human patient.

8. The method of claim 7, wherein the human patient has a history of HAE.

9. The method of claim 1, wherein the therapeutic agent is lanadelumab, ecallantide, icatibant, or human plasma-derived C1 esterase inhibitor.

10. A method for analyzing a sample, comprising:
  (i) providing a biological sample obtained from a subject having, suspected of having, or being at risk for hereditary angioedema (HAE);
  (ii) measuring the level of a RNA biomarker set, wherein the RNA biomarker set comprises a messenger RNA encoding mitochondrially-encoded cytochrome C oxidase III (MT-CO3);
  (iii) identifying the subject as a subject at risk of HAE attack based on the level of the RNA biomarker set, an increase of the level of MT-CO3 of the subject from that of a control subject being indicative that the subject is at risk of HAE attack; and
  (iv) administering to the subject identified as being at risk of HAE attack in step (iii) an effective amount of a therapeutic agent,
  wherein the therapeutic agent is a plasma kallikrein (pKal) inhibitor, a bradykinin 2 receptor (B2R) inhibitor, and/or a C1 esterase inhibitor.

11. The method of claim 10, wherein the therapeutic agent is lanadelumab, ecallantide, icatibant, or human plasma-derived C1 esterase inhibitor.

12. The method of claim 1, wherein the level of the RNA biomarker set or level of MT-CO3 of the subject is at least 1.1-fold higher than the level of the corresponding RNA biomarker or RNA biomarker set obtained from a control subject.

13. The method of claim 1, wherein the level of the RNA biomarker set or level of MT-CO3 of the subject is at least 2-fold higher than the level of the corresponding RNA biomarker or RNA biomarker set obtained from a control subject.

14. The method of claim 10, wherein the biomarker set consists of 2-10 RNA biomarkers.

15. The method of claim 10, wherein the biological sample is a serum sample or a plasma sample.

16. The method of claim 10, wherein the HAE is type I HAE or type II HAE.

17. The method of claim 10, wherein the RNA biomarker set further comprises a microRNA.

18. The method of claim 10, wherein step (ii) involves polymerase chain reaction and/or nucleic acid hybridization.

19. The method of claim 10, wherein the subject is a human patient.

20. The method of claim 19, wherein the human patient has a history of HAE.

21. The method of claim 10, wherein the level of the RNA biomarker set or level of MT-CO3 of the subject is at least 1.1-fold higher than the level of the corresponding RNA biomarker or RNA biomarker set obtained from a control subject.

22. The method of claim 10, wherein the level of the RNA biomarker set or level of MT-CO3 of the subject is at least 2-fold higher than the level of the corresponding RNA biomarker or RNA biomarker set obtained from a control subject.

23. The method of claim 1, wherein the RNA biomarker set further comprises a messenger RNA encoding mitochondrially-encoded NADH:ubiquinone oxidoreductase core subunit 3 (MT-ND3).

24. The method of claim 5, wherein the microRNA is selected from the group consisting of hsa-miR-16-5p, hsa-miR-19a-3p, hsa-miR-20a-5p, hsa-miR-17-5p, hsa-miR-28-5p, hsa-miR-423-3p, hsa-miR-26a-5p, hsa-miR-1307-3p, hsa-miR-335-3p, hsa-miR-139-5p, hsa-miR-485-5p, hsa-miR-26b-5p, hsa-miR-885-5p, hsa-miR-361-3p, hsa-miR-769-5p, hsa-miR-140-5p, hsa-miR-485-3p, hsa-miR-889-3p, hsa-miR-941, RPL23, hsa-miR-328-3p, and hsa-miR-484.

25. The method of claim 10, wherein the RNA biomarker set further comprises a messenger RNA encoding mitochondrially-encoded NADH:ubiquinone oxidoreductase core subunit 3 (MT-ND3).

26. The method of claim 17, wherein the microRNA is selected from the group consisting of hsa-miR-16-5p, hsa-miR-19a-3p, hsa-miR-20a-5p, hsa-miR-17-5p, hsa-miR-28-5p, hsa-miR-423-3p, hsa-miR-26a-5p, hsa-miR-1307-3p, hsa-miR-335-3p, hsa-miR-139-5p, hsa-miR-485-5p, hsa-miR-26b-5p, hsa-miR-885-5p, hsa-miR-361-3p, hsa-miR-769-5p, hsa-miR-140-5p, hsa-miR-485-3p, hsa-miR-889-3p, hsa-miR-941, RPL23, hsa-miR-328-3p, and hsa-miR-484.

\* \* \* \* \*

SEQUENCE LISTING

```
<160> NUMBER OF SEQ ID NOS: 5

<210> SEQ ID NO 1
<211> LENGTH: 304
<212> TYPE: PRT
<213> ORGANISM: Homo sapiens

<400> SEQUENCE: 1

Met Ile Tyr Thr Met Lys Lys Val His Ala Leu Trp Ala Ser Val Cys
1               5                   10                  15
```

-continued

```
Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285

Lys Gln Arg Val Lys Ile Ala Tyr Glu Glu Ile Phe Val Lys Asn Met
290                 295                 300

<210> SEQ ID NO 2
<211> LENGTH: 58
<212> TYPE: PRT
<213> ORGANISM: Homo sapiens

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 60
<212> TYPE: PRT
```

```
<213> ORGANISM: Artificial Sequence
<220> FEATURE:
<223> OTHER INFORMATION: Synthetic polypeptide

<400> SEQUENCE: 3

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 4
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
        115                 120

<210> SEQ ID NO 5
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95
```

```
Phe Gly Gln Gly Thr Lys Val Glu Ile
        100                 105
```